United States Patent
Ishibashi et al.

(10) Patent No.: US 6,638,534 B1
(45) Date of Patent: Oct. 28, 2003

(54) PREPARATION CAPABLE OF RELEASING DRUG AT TARGET SITE IN INTESTINE

(75) Inventors: Takashi Ishibashi, Sakai (JP); Hiroaki Kubo, Kobe (JP); Hiroyuki Yoshino, Suita (JP); Masakazu Mizobe, Takatsuki (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/744,653
(22) PCT Filed: Jul. 26, 1999
(86) PCT No.: PCT/JP99/03989
§ 371 (c)(1),
(2), (4) Date: Jan. 29, 2001
(87) PCT Pub. No.: WO00/06128
PCT Pub. Date: Feb. 10, 2000

(30) Foreign Application Priority Data

Jul. 28, 1998 (JP) .......................................... 10-211678

(51) Int. Cl.[7] ............................. A61K 9/22; A61K 9/32; A61K 9/36; A61K 9/42
(52) U.S. Cl. ..................... 424/482; 424/476; 424/468; 424/480; 424/494; 424/497; 424/498
(58) Field of Search ................................ 424/480, 482, 424/476, 493, 494, 497, 498, 468

(56) References Cited

U.S. PATENT DOCUMENTS

| | | |
|---|---|---|
| 4,496,553 A | 1/1985 | Halskov |
| 4,980,173 A | 12/1990 | Halskov |
| 5,217,720 A | 6/1993 | Sekigawa et al. |
| 5,541,170 A | 7/1996 | Rhodes et al. |
| 5,541,171 A | 7/1996 | Rhodes et al. |

FOREIGN PATENT DOCUMENTS

| | | |
|---|---|---|
| EP | 0 195 476 | 3/1986 |
| EP | 195476 A2 | 9/1986 |
| EP | 0 425 699 | 5/1990 |
| EP | 0 671 168 | 3/1995 |
| EP | 671168 A1 | 9/1995 |

(List continued on next page.)

OTHER PUBLICATIONS

Saffran et al., "A New Approach to the Oral Administration of Insulin and Other Peptide Drugs", Science, Sep. 5, 1986, pp. 1081–1084, vol. 233.

Ishino et al., "Design and Preparation of Pulsatile Release Tablet as a New Oral Drug Delivery System", Chemical & Pharmaceutical Bulletin, 1992, pp. 3036–3041, vol. 40(11), Japan.

(List continued on next page.)

Primary Examiner—James M. Spear
(74) Attorney, Agent, or Firm—Browdy and Neimark, P.L.L.C.

(57) ABSTRACT

A preparation capable of releasing a medicinal substance at a targeted site in the intestine, wherein the preparation dose not releases medicinal substance in endogastri at all, but can quickly release a medicinal substance when it reaches the desired site in the intestine after a certain period of time from discharge of the preparation from the stomach, and wherein a core material containing a medicinal substance is coated with a mixed film of a hydrophobic organic compound—an enteric polymer. The preparation is useful for a local therapy of inflammatory disease in the intestine such as ulcerative colitis or Crohn's disease, or an oral administrative therapy with a medicinal substance of a peptide which is apt to be decomposed chemically or enzymatically in any site except for a specific site in the intestine such as the large intestine, or with a medicinal substance whose absorption site in the intestine is limited, or the like, because a medicinal substance can be delivered selectively to a specific site in the intestine.

25 Claims, 6 Drawing Sheets

FOREIGN PATENT DOCUMENTS

| | | |
|---|---|---|
| JP | 256166/1994 | 9/1994 |
| JP | 8-143476 | 6/1996 |
| JP | 143476/1996 | 6/1996 |
| JP | 10-120571 | 5/1998 |
| JP | 10-191904 | 7/1998 |

OTHER PUBLICATIONS

Theeuwes et al., "Systems for Triggered, Pulsed, and Programmed Drug Delivery", *Annals New York Academy of Sciences*, 1991, pp. 428–440.

Wilding, Iain R., *A Scintigraphic Study to Evaluate What Happens to Pentasa® and Asacol® in the Human Gut*, Practical Gastroenterology, Nov. 1999, pp. 1–8.

PREPARATION CAPABLE OF RELEASING DRUG AT TARGET SITE IN INTESTINE

The present application is the national stage under 35 U.S.C. 371 of PCT/JP99/03989, filed Jul. 26, 1999.

TECHNICAL FIELD

The present invention relates to a preparation capable of releasing a medicinal substance at a targeted site in the intestine, which can selectively deliver a medicinal substance to the large intestine and the like, and a method for preparation thereof.

BACKGROUND ART

Selective delivery of a medicinal substance to a specific site in the intestine has been desired in pharmacotherapy, for example, a local therapy for inflammatory disease in the gastrointestinal tract such as ulcerative colitis or Crohn's disease, an oral administrative therapy with a medicinal substance of a peptide which is apt to be decomposed chemically or enzymatically in any site except for a specific site in the intestine such as the large intestine, or with a medicinal substance whose absorption site in intestine is limited, or the like.

In order to efficiently realize the selective delivery of a medicinal substance in the intestine, it is necessary to design a preparation considering the physical and physiological environment in the human gastrointestinal tract and the traveling time of the preparation through the gastrointestinal tract. With respect to the physical and physiological environment in the gastrointestinal tract, it is recognized that the value of pH in the stomach is usually 1.8 to 4.5 and the value of pH in the intestine is 6.5 to 7.5 in a healthy human. According to the results of the widespread research of Davis et al., in a human, the residence time of a preparation in the stomach is 0.5 to 10 hours and further not only the interindividual variation thereof is large, but also the residence time is considerably influenced, for example, by a condition of feeding, a size of the preparation to be administered and the like, while the traveling time of a preparation through the small intestine is generally recognized to be 3±1 hours and the variation is relatively small (Journal of Controlled Release, 2, 27–38 (1985)).

With respect to a preparation which can selectively deliver a medicinal substance to a specific site in the intestine, hitherto various researches have been done. There have been proposed a preparation wherein a sustained release preparation is coated with an enteric film (Theeuwes et al, Annals of the New York Academy of Science, 618, 428–440 (1991)), a preparation utilizing a technique for controlling the starting time of the release (Ishino et al, Chemical & Pharmaceutical Bulletin, 40, 3036–3041 (1992), Japanese Unexamined Patent Publication No. 72417/1991, Japanese Unexamined Patent Publication No. 256166/1994) and the like, as well as an enteric preparation and a sustained release preparation.

However, in case of using an enteric preparation, since the medicinal substance is released rapidly at the upper small intestine, almost of the medicinal substance is wasted by absorption or decomposition before the medicinal substance is delivered to the targeted site in the intestine. In case of using the sustained release preparation, since the medicinal substance is released gradually, a considerable amount of the medicinal substance is released during the stay of the preparation in the stomach and during the passing of the preparation through the intestine to the targeted site. Further, an attempt to suppress an endogastric releasing of a medicinal substance by coating a sustained release preparation with an enteric film has not completely solved a problem of releasing of a medicinal substance during the passing through the intestine to the targeted site.

Furthermore, recently there has been proposed a method for selectively releasing at the large intestine a medicinal active ingredient coated or matrixed with a polymer, which is specifically decomposed by enterobacteria, such as chitosan and azopolymers, (U.S. Pat. No. 5,217,720; Saffran, Science, 233, 1081–1084 (1986)). However, in this method, the decomposition rate of the polymer cannot be controlled and the delivery to any site other than the large intestine is principally impossible, though this method is preferable as to the selectivity of a release site. For practical use, there are still many problems as regarding the safety and the productivity of the polymer itself because the polymer has never been administered to humans.

Meanwhile, diltiazem hydrochloride granule coated with a mixed film of stearic acid and Eudragit RS is known as a preparation coated with a film containing a hydrophobic organic compound (Japanese Unexamined Patent Publication No. 120571/1998). A preparation coated with a mixed film of a hydrophobic organic compound and an enteric polymer is unknown. Further, the above-mentioned diltiazem hydrochloride granule is not with the intention of releasing a medicinal substance at a desired site in the intestine but a sustained release preparation for sustainably releasing a medicinal substance after dosage thereof.

The present invention aims to provide a highly practicable preparation for oral administration capable of selectively delivering a medicinal substance at any site in the intestine by not using an extraordinary material but using a safe raw material usually used for pharmaceutical preparation.

DISCLOSURE OF THE INVENTION

As the abovementioned problems, the inventors have found that a preparation in which a core material containing a medicinal substance coated with a mixed film of hydrophobic organic compound-enteric polymer, has a unique releasing behavior in that the preparation releases no medicinal substance in an acidic solution but releases a medicinal substance quickly in a neutral or basic solution after a certain period of time (lag-time). The inventors have also found that the lag-time can be controlled by changing the coating amount of film and the ratio of the amount of the hydrophobic organic compound to the amount of the enteric polymer.

According to a preparation of the present invention, a medicinal substance is not released in an acidic condition such as endogastric condition after dosage. The medicinal substance is not released at all during a certain period of time, even though the preparation is discharged from the stomach and the value of pH changes into a neutral or weakly acidic condition. The medicinal substance can be released when the preparation reaches the targeted site in the intestine after said certain period.

Namely, the invention is a preparation capable of releasing a medicinal substance at a targeted site in the intestine, wherein a core material containing a medicinal substance is coated with a mixed film of a hydrophobic organic compound and an enteric polymer or shellac.

The invention is further directed to such a preparation in which the hydrophobic organic compound is one or more of a higher fatty acid having 6 to 22 carbon atoms which may have an unsaturated bond, a higher alcohol having 6 to 22 carbon atoms which may have an unsaturated bond, a triglyceride of the higher fatty acid having 6 to 22 carbon atoms which may have an unsaturated bond, and a natural fat which may be hydrogenated; and in which the enteric polymer is one or more of an enteric cellulose derivative, an enteric acrylic copolymer, an enteric maleic copolymer, and an enteric polyvinyl derivative.

The invention is still further directed to such a preparation in which the higher fatty acid having 6 to 22 carbon atoms which may have an unsaturated bond is stearic acid, lauric acid, myristic acid, palmitic acid, or behenic acid; the higher alcohol having 6 to 22 carbon atoms which may have an unsaturated bond is lauryl alcohol, myristyl alcohol, cetyl alcohol, stearyl alcohol, or behenyl alcohol; the triglyceride of the fatty acid having 6 to 22 carbon atoms which may have an unsaturated bond is glyceryl tristearate, glyceryl trimyristate, glyceryl tripalmitate, or glyceryl trilaurate; the natural fat which may be hydrogenated is hydrogenated castor oil, hydrogenated coconut oil, or beef tallow; the enteric cellulose derivative is hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose or ethylhydroxyethylcellulose phthalate; the enteric acrylic copolymer is styrene.acrylic acid copolymer, methyl acrylate.acrylic acid copolymer, methyl acrylate.methacrylic acid copolymer, butyl acrylate.styrene.acrylic acid copolymer, methacrylic acid.methyl methacrylate copolymer, methacrylic acid.ethyl acrylate copolymer, or methyl acrylate.methacrylic acid.octyl acrylate copolymer; the enteric maleic copolymer is vinylacetate.maleic acid anhydride copolymer, styrene.maleic acid anhydride copolymer, styrene.maleic acid monoester copolymer, vinylmethylether.maleic acid anhydride copolymer, ethylene.maleic acid anhydride copolymer, vinylbutylether.maleic acid anhydride copolymer, acrylonitrile.methyl acrylate.maleic acid anhydride copolymer, or butyl acrylate.styrene.maleic acid anhydride copolymer; and the enteric polyvinyl derivative is polyvinyl alcohol phthalate, polyvinylacetal phthalate, polyvinyl butylate phthalate, or polyvinylacetoacetal phthalate.

The invention still further relates to such a prepaaration in which the hidrophobic organic compound is steaaric acid and the enteric polymer is methacrilic acid.methyl methacrylate copolymer.

A further embodiment of the invention relates to such a preparation in which the mixing ratio of the amount of the hydrophobic organic compound to the amount of the enteric polymer in the mixed film of hydrophobic organic compound—enteric polymer is within a range of 30:70 to 80:20.

A still further embodiment of the invention is such a preparation in which the coating ratio of the mixed film of hydrophobic organic compound—enteric polymer is within a range of 20 to 100% by weight.

Yet a further embodiment of the invention is such a preparation in which the medicinal substance is not released during at least 10 hours in the first fluid of the disintegration test in Japanese Pharmacopoeia XIII and is not released during at least 2 hours in the second fluid of the disintegration test in Japanese Pharmacopoeia XIII.

Another embodiment of the invention is a method for preparing a pharmaceutical preparation capable of releasing a medicinal substance at a targeted site in the intestine, wherein a core material containing a medicinal substance is spray-coated with a coating solution in which a hydrophobic organic compound and an enteric poltner are dissolved in a same solvent.

BEST MODE FOR CARRYING OUT THE INVENTION

In the present invention, hydrophobic organic compound means a hydrophobic organic compound that excludes polymers and that does not have salt formation. Examples of the hydrophobic organic compound include a higher fatty acid having 6 to 22 carbon atoms which may have an unsaturated bond, a higher alcohol having 6 to 22 carbon atoms which may have an unsaturated bond, a triglyceride of higher fatty acid having 6 to 22 carbon atoms which may have an unsaturated bond, a natural fat which may be hydrogenated, and the like.

Examples of the higher fatty acid having 6 to 22 carbon atoms which may have an unsaturated bond include stearic acid, lauric acid, myristic acid, palmitic acid, behenic acid and the like. Examples of the higher alcohol having 6 to 22 carbon atoms which may have an unsaturated bond include lauryl alcohol, myristyl alcohol, cetyl alcohol, stearyl alcohol, behenyl alcohol and the like. Examples of the triglyceride of the higher fatty acid having 6 to 22 carbon atoms which may have an unsaturated bond include the triglyceride of the above-mentioned higher fatty acid such as glyceryl tristearate, glyceryl trimyristate, glyceryl tripalmitate and glyceryl trilaurate, and the like. Examples of the natural fat which may be hydrogenated include hydrogenated castor oil, hydrogenated coconut oil, beef tallow and the like. Among these examples, stearic acid and palmitic acid are particularly preferable. Further, stearic acid is most preferable.

In the present invention, the above-mentioned hydrophobic organic compound may be employed not only alone but also in a mixture of two or more thereof.

Further, the enteric polymer employed in the present invention may be a polymer which does not dissolve in an acidic solution and does dissolve in a neutral or basic solution, for example, a solution in which the value of pH is at least 5, more preferably at least 6.0, further more preferably at least 6.5. Examples of the enteric polymer include an enteric cellulose derivative, an enteric acrylic copolymer, an enteric maleic copolymer, an enteric polyvinyl derivative, and the like. Shellac may be used as an alternative to the enteric polymer.

Concrete examples of the above-mentioned enteric cellulose derivative include hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate and the like. Concrete examples of the enteric acrylic copolymer include styrene.acrylic acid copolymer, methyl acrylate.acrylic acid copolymer, methyl acrylate-.methacrylic acid copolymer, butyl acrylate.styrene.acrylic acid copolymer, methacrylic acid.methyl methacrylate copolymer (e.g. Trade-names: Eudragit L 100 and Eudragit S, available from Röhm Pharma), methacrylic acid ethyl acrylate copolymer (e.g. Trade-name: Eudragit L 100-55, available from Röhm Pharma), methyl acrylate methacrylic acid octyl acrylate copolymer and the like. Concrete examples of the enteric maleic copolymer include vinylacetate maleic acid anhydride copolymer, styrene maleic acid anhydride copolymer, styrene.maleic acid monoester copolymer, vinylmethylether maleic acid anhydride copolymer, ethylene.maleic acid anhydride copolymer, vinylbutylether.maleic acid anhydride copolymer, acrylonitrile.methyl acrylate maleic acid anhydride copolymer, butyl acrylate.styrene.maleic acid anhydride copolymer and the like. Concrete examples of the enteric polyvinyl derivative include polyvinyl alcohol phthalate, polyvinylacetal phthalate, polyvinyl butylate phthalate, polyvinylacetoacetal phthalate and the like. Among these examples, methacrylic acid.methylmethacrylate copolymer and methacrylic acid-.ethylacrylate copolymer are preferable, and methacrylic acid.methylmethacrylate copolymer is more preferable.

In the present invention, the above-mentioned enteric polymer may be employed not only alone but also in a mixture of two or more thereof.

In a mixed film of hydrophobic organic compound—enteric polymer, examples of the combination of a hydrophobic organic compound and an enteric polymer include higher fatty acid having 6 to 22 carbon atoms which may have an unsaturated bond—enteric cellulose derivatives (for example, stearic acid—hydroxypropylmethylcellulose acetate saccinate, stearic acid—hydroxypropylmethylcellulose phthalate, behenic acid—hydroxypropylmethylcellulose acetate, behenic—acid hydroxypropylmethylcellulose phthalate and the like); higher fatty acid having 6 to 22 carbon atoms which may have an unsaturated bond—enteric acrylic copolymers (for example, stearic acid—methacrylic acid—methyl methacrylate copolymer, palmitic acid—methacryl acid.methyl methacrylate copolymer, palmitic acid—methacryl acid.ethyl acrylate copolymer, stearic acid—methacrylic acid.ethyl acrylate copolymer and the like); higher fatty acid having 6 to 22 carbon atoms which may have an unsaturated bond—enteric maleic copolymers (for example, stearic acid—vinylacetate.maleic anhydride copolymer, stearic acid—styrene.maleic anhydride copolymer and the like); higher fatty acid having 6 to 22 carbon atoms which may have an unsaturated bond—enteric polyvinyl derivatives (for example, stearic acid—polyvinyl alcohol phthalate, palmitic acid—polyvinyl acetal phthalate and the like); higher fatty acid having 6 to 22 carbon atoms which may have an unsaturated bond—shellacs (for example, palmitic acid—shellac, stearic acid—shellac, behenic acid—shellac and the like); higher alcohol having 6 to 22 carbon atoms which may have an unsaturated bond—enteric cellulose derivatives (for example, stearyl alcohol—hydroxypropylmethylcellulose acetate saccinate, stearyl alcohol—hydroxypropylmethylcellulose phthalate, behenic acid—hydroxypropylmethylcellulose acetate, behenic acid—hydroxypropylmethylcellulose phthalate and the like); higher alcohol having 6 to 22 carbon atoms which may have an unsaturated bond—enteric acrylic copolymers (for example, stearyl alcohol—methacrylic acid.methyl methacrylate copolymer, stearyl alcohol—methacrylic acid.ethyl acrylate copolymer and the like); higher alcohol having 6 to 22 carbon atoms which may have an unsaturated bond—enteric maleic copolymers (for example, stearyl alcohol—vinylacetate maleic acid anhydride copolymer, stearyl alcohol—styrene.maleic acid anhydride copolymer and the like); higher alcohol having 6 to 22 carbon atoms which may have an unsaturated bond—enteric polyvinyl derivatives (for example, stearyl alcohol—polyvinylalcohol phthalate, stearyl alcohol—polyvinylacetal phthalate and the like); higher alcohol having 6 to 22 carbon atoms which may have an unsaturated bond—shellac (for example, stearyl alcohol—shellac, lauryl alcohol—shellac and the like); triglyceride of the higher fatty acid having 6 to 22 carbon atoms which may have an unsaturated bond—enteric cellulose derivatives (for example, glyceryl tristearate hydroxypropylmethylcellulose acetate saccinate, glyceryl tripalmitate—hydroxypropylmethylcellulose acetate saccinate and the like); triglyceride of the higher fatty acid having 6 to 22 carbon atoms which may have an unsaturated bond—enteric acrylic copolymers (for example, glyceryl tristearate—methacrylic acid.methyl methacrylate copolymer, glyceryl tristearate—methacrylic acid.ethyl acrylate copolymer and the like); triglyceride of the higher fatty acid having 6 to 22 carbon atoms which may have an unsaturated bond—enteric maleic copolymers (for example, glyceryl tristearate—vinylacetate.maleic acid anhydride copolymer, glyceryl tristearate—styrene.maleic acid anhydride copolymer and the like); triglyceride of the higher fatty acid having 6 to 22 carbon atoms which may have an unsaturated bond—enteric polyvinyl derivatives (for example, glyceryl tristearate—polyvinylalcohol phthalate, glyceryl tripalmitate—polyvinylacetal phthalate and the like); triglyceride of the higher fatty acid having 6 to 22 carbon atoms which may have an unsaturated bond—shellac (for example, glyceryl tripalmitate—shellac, glyceryl tristearate—shellac and the like); natural fat which may be hydrogenated—enteric cellulose derivatives (for example, hydrogenated castor oil—hydroxypropylmethylcellulose acetate saccinate, beef tallow—hydroxypropylmethylcellulose phthalate and the like); natural fat which may be hydrogenated—enteric acrylic copolymers (for example, hydrogenated castor oil—methacrylic acid.methyl methacrylate copolymer, beef tallow—methacrylic acid.ethyl acrylate copolymer and the like); natural fat which may be hydrogenated—enteric maleic copolymers (for example, hydrogenated castor oil—vinylacetate.maleic acid anhydride copolymer, beef tallow—styrene.maleic acid anhydride copolymer and the like); natural fat which may be hydrogenated—enteric polyvinyl derivatives (for example, hydrogenated castor oil—polyvinylalcohol phthalate, beef tallow—polyvinylacetal phthalate and the like); natural fat which may be hydrogenated—shellac (for example, hydrogenated castor oil—shellac, beef tallow—shellac and the like).

Particularly preferable examples of the above-mentioned combination of a hydrophobic organic compound and an enteric polymer include stearic acid—methacrylic acid.methyl methacrylate copolymer, palmitic acid—methacrylic acid.methyl methacrylate copolymer, stearic acid—methacrylic acid.ethyl acrylate copolymer, palmitic acid—methacrylic acid.ethyl acrylate copolymer, and the like.

A lag-time of a preparation of the present invention (the time until a start of releasing the medicinal substance in a neutral and weak basic solution, i.e. the time from discharging a preparation from the stomach to a start of releasing a medicinal substance when the preparation is orally administrated) can be controlled by controlling a mixing ratio of a hydrophobic organic compound to an enteric polymer in a mixed film and a coating ratio with a mixed film. Namely, the higher the ratio of a hydrophobic organic compound to an enteric polymer in a mixed film is, the longer the lag-time is. And the larger the coating ratio with a mixed film, the longer the lag-time is.

The mixing ratio of a hydrophobic organic compound to an enteric polymer in a mixed film may be freely selected in order to obtain the desired lag-time. The mixing ratio of a hydrophobic organic compound to an enteric polymer in a mixed film may be usually within a range of 5:95 to 95:5 by weight, particularly preferably within a range of 30:70 to 80:20 by weight.

Further, the coated amount with the mixed film may be also freely selected in order to obtain the desired lag-time. The coating ratio (a percent by weight of the mixed film to the core material) may be, for instance, with a range of 5 to 300% by weight, particularly preferably within a range of 20 to 100% by weight, though depending on the kind and size of the core material.

When a dissolution test according to the dissolution test (puddle method) of Japanese Pharmacopoeia XIII (hereinafter referred to as JP) is carried out, the lag-time can be determined as the time until a start of releasing a medicinal substance to the second fluid (pH 6.8) of the disintegration test of JP. By a person skilled in the art, the mixed ratio and the coated amount to obtain the desired lag-time are easily determined by preparing preparations having various mixed ratios and coating ratios. In this case, it is preferable not to release the medicinal substance for 5 hours in the first fluid (pH 1.2) of the disintegration test of JP.

The lag-time may be freely designed according to the desired site at which the medicinal substance is to be delivered. To obtain a successful preparation in accordance with the present invention, it is required that the medicinal substance not be released for at least 2 hours in the second fluid (pH 6.8) of the disintegration test of JP. Namely, the lag-time is preferably at least 2 hours, more preferably at least 3 hours.

The preparations to be intended to release a medicinal substance nearby the lower part of the ileum, the ascending colon and the transverse colon can be obtained when the lag-times are designed to about 3 hours, about 4 hours and about 7 hours, respectively. Further, the preparation to be intended to release a medicinal substance nearby the lower large intestine can be obtained when the lag-time is designed to longer than about 7 hours.

Further, various additives may be mixed into the mixed film of the preparation according to the present invention. As the said additives, a coloring agent, a masking agent, a plasticizer, a lubricant and the like can be mixed.

Examples of the coloring agent include, for instance, a food dye, a lake dye, caramel, carotene, annatto, cochineal, iron dioxide and the like, and an opaque coloring agent, OPALUX, mostly made of a lake dye and syrup. Concrete examples include Food aluminum lakes such as Food red No.2, No.3, yellow No.4, No.5, green No.3, blue No.1, No.2 and purple No.1; annatto (natural color derived from Bixa orellana); carmine (aluminum carminate); pearl essence (of which principal constituent is guanine); and the like.

Examples of the masking agent include, for instance, titanium dioxide, precipitated calcium carbonate, dibasic calcium phosphate, calcium sulfate and the like.

Examples of the plasticizer include, for instance, phthalic derivatives such as diethylphthalate, dibutylphthalate and butylphthalylbutylglycolate, silicone oil, triethylcitrate, triacetine, propylene glycol, polyethyleneglycol and the like.

Examples of the lubricant include, for instance, magnesium stearate, talc, synthetic magnesium silicate, fine grain silicon oxide and the like.

As to the amount of additives and the timing for adding thereof, there is not any problem as long as they are in the range according to the usual knowledge in the field of the preparation technology.

The method for preparing the preparation of the present invention is not limited as long as the desired preparation capable of releasing a medicinal substance at a targeted site in the intestine is obtained. The preparation is easily obtained by a spray-coating to a core material containing a medicinal substance with a coating solution in which a hydrophobic organic compound and an enteric polymer are dissolved in a same solvent.

The solvent of the coating solution is not limited as long as the hydrophobic organic compound and the enteric polymer are soluble therein, for instance, alcohols such as methanol, ethanol, n-propanol, isopropanol, n-butanol, 2-methoxyethanol (Trade-name: METHYL CELLOSOLVE, available from Katayama Chemical Industries Co., Ltd.), and 2-ethoxyethanol (Trade-name: CELLOSOLVE, available from Katayama Chemical Industries Co., Ltd.); hydrocarbons such as hexane, cyclohexane, petroleum ether, petroleum benzin, ligroin, benzene, toluene, and xylene; ketones such as acetone and methylethylketone; hydrocarbon halides such as dichloromethane, chloroform, carbon tetrachloride, ethylene dichloride, trichloroethylene, and 1,1,1-trichloroethane; esters such as methyl acetate, ethyl acetate, and butyl acetate; ethers such as isopropyl ether and dioxane.

The solvent may be selected corresponding to the employed hydrophobic organic compound and the employed enteric polymer, and can be employed in a suitable mixture of two or more solvents.

Among them, alcohols are particularly preferable, and ethanol is more particularly preferable.

Coating may be carried out with a known coating machine. Concrete examples of the coating machine include a fluidized bed coating machine, a centrifugal fluidized bed coating machine, a pan coating machine and the like.

The core particle of the present invention is consisting of a medicinal substance alone, or is consisting of a medicinal substance and various additives for preparations usually employed in the art. The formulation thereof is not particularly limited. Examples of the formulation include a tablet, a capsule and the like, as well as particles such as a grain and a granule. Among them, a grain, granule or a tablet are particularly preferable.

The medicinal substance is not particularly limited as long as it is for an oral administration. Examples of various medicinal substances include (1) antipyretic analgesic anti-inflammatory agents (for example, indomethacin, aspirin, diclofenac sodium, ketoprofen, ibuprofen, mefenamic acid, azulene, phenacetin, isopropylantipyrine, acetaminophen, bendzac, phenylbutazone, flufenamic acid, sodium salicylate, salicylamide, sasapyrine, etodolac, and the like); (2) steroidal anti-inflammatory agents (for example, dexamethasone, hydrocortisone, prednisolone, triamcinolone, and the like); (3) antiulcer agents (for example, 5-amino salicylic acid, ecabet sodium, enprostil, sulpiride, cetraxate hydrochloride, gefarnate, irsogladine maleate, cimetidine, ranitidine hydrochloride, famotidine, nizatidine, roxatidine acetate hydrochloride, and the like); (4) coronary vasodilators (for example, nifedipine, isosorbide dinitrate, diltiazem hydrochloride, trapidil, dipyridamole, dilazep dihydrochloride, verapamil, nicardipine, nicardipine hydrochloride, verapamil hydrochloride, and the like); (5) peripheral vasodilators (for example, ifenprodil tartrate, cinepazet maleate, cyclandelate, cinnarizine, pentoxifylline, and the like); (6) antibiotics (for example, ampicillin, amoxicillin, cephalexin, erythromycin ethylsuccinate, bacampicillin hydrochloride, minocycline hydrochloride, chloramphenicol, tetracycline, erythromycin, ceftazidime, cefuroxime sodium, aspoxicillin, ritipenem acoxil hydrate, and the like); (7) synthetic antimicrobials (for example, nalidixic acid, piromidic acid, pipemidic acid trihydrate, enoxacin, cinoxacin, ofloxacin, norfloxacin, ciprofloxacin hydrocloride, sulfamethoxazole trimethoprim, and the like); (8) antiviral agents (for example, aciclovir, ganciclovir, and the like); (9) antispasmodics (for example, propantheline bromide, atropine sulfate, oxapium bromide, timepidium bromide, butylscopolamine bromide, trospium chloride, butropium bromide, N-methyl scopolamine methyl sulfate, methyloctatropine bromide, and the like); (10) antitussives (for example, tipepidine hibenzoate, methylephedrine hydrochloride, codeine phosphate, tranilast, dextromethorphan hydrobromide, dimemorfan phosphate, clobutinol hydrochloride, fominoben hydrochloride, benproperine phosphate, eprazinone hydrochloride, chlophedianol hydrochloride, ephedrine hydrochloride, noscapine, pentoxyverine citrate, oxeladine citrate, isoaminil citrate, and the like); (11) expectorants (for example, bromhexine hydrochloride, carbocysteine, ethylcysteine hydrochloride, methylcysteine hydrochloride, and the like); (12) bronchodilators (for example, theopylline, aminophylline, disodium cromoglycate, procaterol hydrochloride, trimetoquinol hydrochloride, diprophylline, salbutamol sulfate, clorprenaline hydrochloride, formoterol fumarate, orciprenalin sulfate, pirbuterol hydrochloride, hexoprenaline sulfate, bitolterol mesilate, clenbuterol hydrochloride, terbutaline sulfate, mabuterol hydrochloride, fenoterol hydrobromide, methoxy phenamine hydrochloride, and the like); (13) cardiacs (for example, dopamine hydrochloride, dobutamine hydrochloride, docarpamine, denopamine, caffeine, digoxin, digitoxin, ubidecarenon, and the like); (14) diuretics (for example, furusemide, acetazolamide, trichlormethiazide, methylclothiazide, hydrochlorothiazide, hydroflumethiazide, ethiazide, cyclopenthiazide, spironolactone, trimterene, fluorothiazide, piretanide, mefruside, ethacrynic acid, azosemido, clofenamide, and the like); (15) muscle relaxants (for example, chlorphenesin carbamate, tolperisone hydrochloride, eperisone hydrochloride, tizanidine hydrochloride, mephenesin, chlorzoxazone, phenprobamate, methocarbamol, cllormezanone, pridinol mesylate, afloqualone, baclofen, dantrolene sodium, and the like); (16) brain metabolism improvers (for example, nicergoline, meclofenoxate hydrochloride, taltirelin, and the like); (17) minor tranquilizers (for example, oxazolam, diazepam, clotiazepam, medazepam, temazepam, fludiazopam, meprobamate, nitrazopam, chlordiazopoxide, and the like); (18) major tranquilizers (for example, sulpiride, clocapramin hydrochloride, zotepine, chlorpromazine, haloperidol, and the like); (19) β-blockers (for example, bisoprolol fumarate, pindolol, propranolol hydrochloride, carteolol hydrochloride, metoprolol tartrate, labetalol hydrochloride, acebutolol hydrochloride, bufetolol hydrochloride, alprenolol hydrochloride, arotinolol hydrochloride, oxprenolol hydrochloride, nadolol, bucumolol hydrochloride, indenolol hydrochloride, timolol maleate, befunolol hydrochloride, bupranolol hydrochloride, and the like); (20) antiarrhythmic agents (for example, procainamide hydrochloride, disopyramide, ajmaline, quinidine sulfate, aprindine hydrochloride, propaphenone hydrochloride, mexiletine hydrochloride, azimilide hydrochloride, and the like); (21) antipodagrics (for example, allopurinol, probenecid, colchicine, sulfinpyrazone, benzbromarone, bucolome, and the Like); (22) anticoagulants (for example, ticlopidine hydrochloride, dicumarol, warfarin potassium, (2R,3R)-3-acetoxy-5-[2-(dimethylamino)ethyl]-2,3-dihydro-8-methyl-2-(4-methylphenyl)-1,5-benzothiazepine-4(5H)-on-maleate, and the like); (23) thrombolytic agents (for example, methyl (2E,3Z)-3-benzyliden-4-(3,5-dimethoxy-α-methylbenzyliden)-N-(4-methylpiperazine-1-yl) succinamate.hydrochloride, and the like); (24) agents for liver disease (for example, (±)r-5-hydroxymethyl-t-7-(3,4-dimethoxyphenyl)-4-oxo-4,5,6,7-tetrahydrobenzo[b]furan-c-6-carbonate lactone, and the like); (25) antiepileptics (for example, phenytoin, sodium valproate, metharbital, carbamazepine, and the like); (26) antihistamines (for example, chlorpheniramine maleate, clemastine fumarate, mequitazine, alimemazine tartrate, cycloheptazine hydrochloride, bepotastine besylate, and the like); (27) antiemetics (for example, difenidol hydrochloride, metoclopramide, donperidone, betahistine mesylate, trimebutine maleate, and the like); (28) hypotensive agents (for example, dimethylaminoethylreserpinate dihydrochloride, recinnamine, methyldopa, prazosin hydrochloride, bunazosin hydrochloride, clonidine hydrochloride, budralazine, urapidil, N-[6-[2-[(5-bromo-2-pyrimidinyl) oxy]ethoxy]-5-(4-methylphenyl)-4-pyrimidinyl]-4-(2-hydroxy-1,1-dimethylethyl)benzensufoneamlde sodium salt, and the like); (29) agents for hyperlipemia (for example, pravastatin sodium, fluvastatin sodium, and the like); (30) sympathomimetic agents (for example, dihydroergotamine mesylate, isoproterenol hydrochloride, etilefrine hydrochloride, and the like); (31) oral antidiabetics (for example, glibenclamide, tolbutamide, glymidine sodium, and the like); (32) oral carcinostatic agents (for example, marimastat, and the like); (33) alkaloid narcotic (for example, morphine, codeine, cocaine, and the like); (34) vitamins (for example, vitamin B1, vitamin B2, vitamin B6, vitamin B12, vitamin C, folic acid, and the like); (35) agents for treatment of pollakisuria (for example, flavoxate hydrochloride, oxybutynin hydrochloride, terodiline hydrochloride, and the like); (36) angiotensin converting enzyme inhibitors (for example, imidapril hydrochloride, enalapril maleate, alacepril, delapril hydrochloride, and the like); or the like.

Since the medicinal substance can be delivered to the large intestine according to the preparation of the present invention, among the above-mentioned medicinal substance, therapeutic agents for ulcerative colitis and Crohn's disease such as 5-aminosalicylic acid and prednisolone are particularly preferable. Further, a peptide such as insulin which dose not usually employed for an oral administration may be employed as well as the above-mentioned medicinal substance.

The additive for preparations is not limited and all additives can be employed suitably as long as the additives can be employed for a solid preparation.

Examples of the additives include, for instance, vehicles such as lactose, saccharose, mannitol, xylitol, erythritol, sorbitol, maltitol, calcium citrate, calcium phosphate and microcrystalline cellulose; disintegrants such as corn starch, potato starch, sodium carboxymethyl starch, partly pregelatinized starch, carboxymethylcellulose calcium, carboxymethylcellulose, low substituted hydroxypropylcellulose, crosslinked carboxymethylcellulose sodium and crosslinked polyvinylpyrrolidone; binders such as hydroxypropylcellulose, hydroxypropylmethylcellulo se, polyvinylpyrrolidone, polyethyleneglycol, dextrin and pregelatinized starch; lubricants such as magnesium stearate, calcium stearate, talc, light anhydrous silicic acid and hydrated silicon dioxide; further, surface active agents such as phospholipid, glycerin ester of fatty acid, sorbitan ester of fatty acid, polyoxyethylene ester of fatty acid, polyethyleneglycol ester of fatty acid, polyoxyethlene hydrogenated castor oil, polyoxyethlene alkylether and sucrose ester of fatty acid; furthermore, aromatics such as orange and strawberry, coloring matters such as sesqui-iron oxide, yellow sesqui-iron oxide, Food yellow No.5, Food yellow No.4 and aluminum chelate; sweetening agents such as saccharin and aspartame; corrigents such as citric acid, sodium citrate, succinic acid, tartaric acid, fumaric acid and glutamic acid; solubilizing agents such as cyclodextrin, arginine, lysine and trisaminomethane.

When grains or granules are employed as a core particle, they can be prepared by known methods for granulation such as wet granulation, dry granulation, layering granulation and impregnate granulation.

In wet granulation, according to a usual method, granulation/grading may be carried out by granulating with an agitating granulator, a high speed mixer granulator, or the like, after adding a binder solution to a mixture in which a medicinal substance is mixed with various additives for preparations, or by employing an oscillating granulating machine after kneading and adding a binding solution to a mixture of a medicinal substance and various additives for preparations. Further, granulation can be carried out by employing a fluidized bed granulator, agitation fluidized bed granulator, or the like, with spraying a binder solution to a fluidizing mixture of a medicinal substance and various additives for preparations.

In dry granulation, a mixture of a medicinal substance and various additives for preparations may be granulated by employing a roller compactor, a roll granulator and the like.

In case of preparation using a layering granulation, it would suffice to add a medicinal substance (if necessary, together with other pharmaceutical additive) onto a rotating inert carrier while a binder solution is being sprayed, using a centrifugal fluidized bed coater or the like, thereby adhering the medicinal substance onto the carrier. In this case, the medicinal substance may be attached onto the carrier using, instead of the binder solution, a substance capable of melting by heating (heat melting substance) such as fats and oils, or wax, which is melted by adding together with the medicinal substance under heating.

In case of preparation using layerring granulation, it would suffice to add a medicinal substance (if necessary, toguther with other pharmaceutical additice) onto a rotating inert carrier while a binder solution is being sprayed, using a centrifungal fluidized bed coater or the like, thereby adhering the medicinal substance onto the carrier. In this case, the medicinal substance may be attached onto the carrier using, instead of the binder solution, a substance capable of melting by heating (heat melting substance) such as fats and oils, or wax, which is melted by adding together with the medicinal substance under heating.

Examples of the inert carrier include, for instance, crystallines of sugars or inorganic salts such as crystalline of lactose, microcrystalline cellulose, crystalline of sodium chloride, a spherical granulated material (such as the spherical granulated material of crystalline cellulose (available from Asahi Chemical Industry Co., Ltd.; Trade-name: Avicel SP), the spherical granulated material of crystalline cellulose and lactose (available from Freund Industrial Co., Ltd.; Trade-name: Nonpareil NP-5, and Nonpareil NP-7), the spherical granulated material of refined sugar (available from Freund Industrial Co., Ltd.; Trade-name: Nonpareil-103), the spherical granulated material of lactose and α-starch).

In impregnating granulation, suitable concentration of medicinal substance solution is mixed with a porous carrier in order to keep the medicinal substance solution into the pore portion of the carrier, and then the mixture may be dried in order to remove the solvent.

Examples of a porous carrier include, for instance, aluminum magnesium metasilicate (available from Fuji Chemical Industry Co., Ltd.; Trade-name: NEUSILIN), calcium silicate (available from Eisai Co., Ltd.; Trade-name: FLORITE) and the like.

When a tablet is used as a core material, mixture of a medicinal substance and various pharmaceutical additives is press-formed as such, or disintegrator, lubricant and the like are added to the mixture after forming a granulated product with the above-mentioned method to form a tablet.

When a capsule is used as a core material, hard capsule or soft capsule which is filled with a medicinal substance may be used as such.

Further, in a preparation of the present invention, a layer comprising a material such as water-soluble material, water-insoluble material, gastrosoluble material can be provided between a core material and a mixed film of hydrophobic organic compound—enteric polymer in order to prevent interaction of the medicinal substance and the mixed film, or to control the releasing rate after starting release of the medicinal substance.

Examples of the water-soluble material include, for instance, water-soluble cellulose ethers such as methylcellulose, hydroxypropylcellulose and hydroxypropylmethylcellulose; water-soluble polyvinyl derivatives such as polyvinyl pyrrolidone and polyvinylalchol; alkylene oxide polymers such as polyethyleneglycol. Examples of the water-insoluble material include water insoluble cellulose ethers such as ethylcellulose; water insoluble acrylic copolymers such as ethyl acrylate.methyl methacrylate.trimethylammoniumethyl methacrylate chloride copolymer (for instance, available from Rbhm Pharma; Trade-name: Eudragit RS) and methyl methacrylate.ethyl acrylate copolymer (for instance, available from Röhm Pharma; Trade-name: Eudragit NE30D), hydrogenated oils and the like. Examples of gastrosoluble material include gastrosoluble polyvinyl derivative such as polyvinylacetal diethylaminoacetate, gastrosoluble acrylic copolymer such as methyl methacrylate butyl methacrylate.dimethylamino-ethyl methacrylate copolymer (for instance, available from Röhm Pharma; Trade-name: Eudragit E), and the like.

The preparation of the present invention obtained can be used as a preparation for oral administration as such. In case of using grains or granules as a core material, it can be formed into various dosage forms which are suitable for oral administration form, as well as obtaining a tablet by press-forming or a capsule by filling into a capsule after adding various pharmaceutical additive to the coated granule (or grain) obtained as the need arises.

The present invention is further explained in details based on the comparative example and the examples as follows, but is not limited thereto.

EXAMPLE 1

The layering granulation was carried out by adding the mixture of 200 g of 5-amino salicylic acid and 30 g of low substituted hydroxypropylcellose (grade: LH-20, available from The Shin-etsu Chemical Industry Co., Ltd.) to 60 g of Nonpareil—103 (available from Freund Industrial Co., Ltd.) with spraying 20% by weight of sucrose solution (solvent: mixture of water—ethanol (content of ethanol is 25% by weight)) as a binder, using a centrifugal fluidized bed coater (CF, made by Freund Industrial Co., Ltd.). The plain granule was obtained.

A coating solution was prepared by dissolving 8 g of Eudragit L 100 (methacrylic acid methylmethacrylate copolymer, available from Röhm Pharma) and 8 g of stearic acid (available from Snow Brand Milk Products Co., Ltd.) into 184 g of ethanol. Using a centrifugal fluidized bed coater, 50 g of the plain granule were coated with the solution by spraying to obtain the granule coated with the mixed film of stearic acid—Eudragit L 100 having coating ratio of 30% by weight.

With respect to the coated granule obtained, the disintegration test was carried out with the first fluid (pH 1.2) and the second fluid (pH 6.8) of the disintegration test in JP according to the method of the disintegration test (puddle method) in JP, at 37° C. and at the rotation speed of 100 rpm. The result was shown in FIG. 1.

Figure 1:
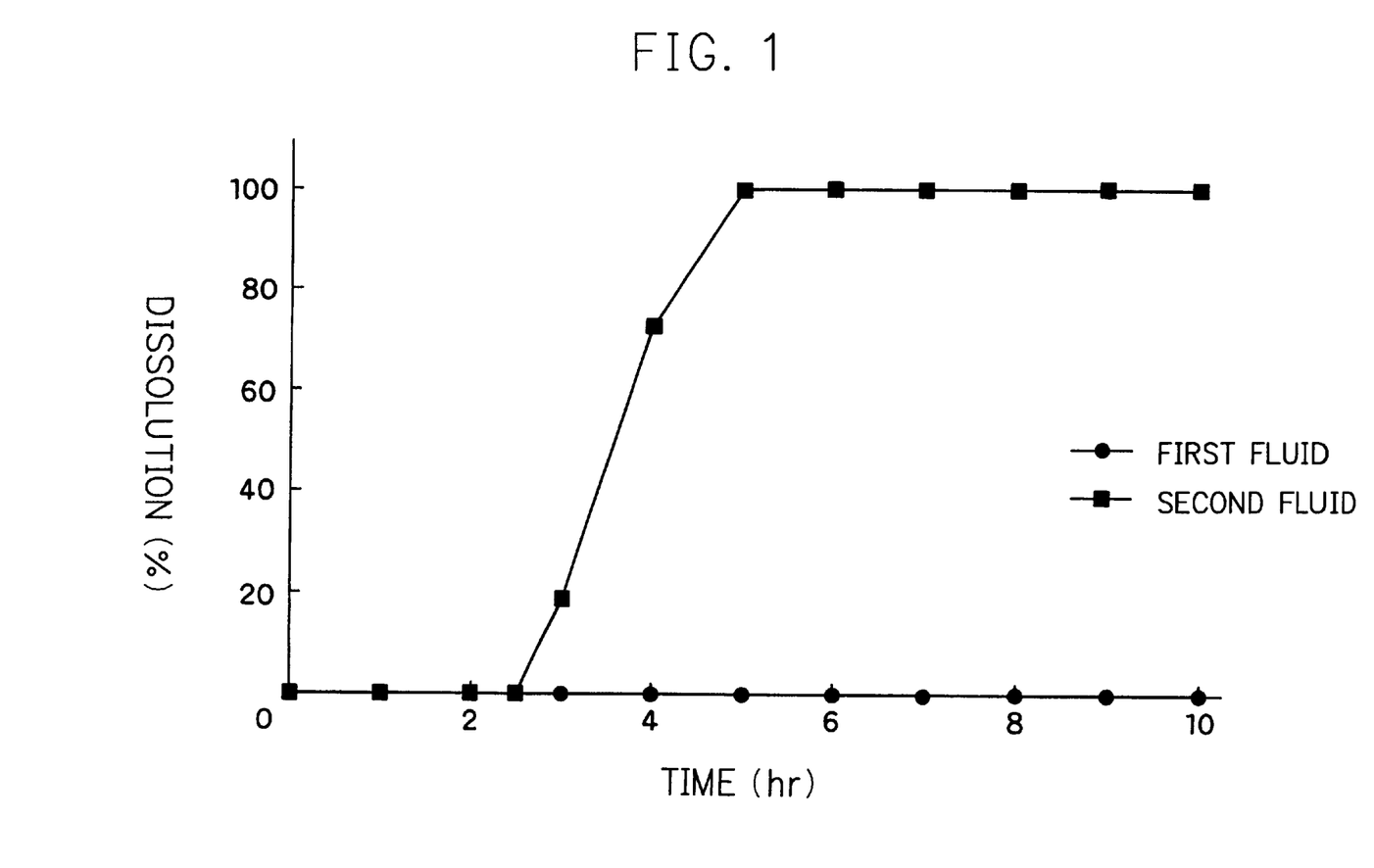
FIG. 1 is a graph showing the 5-aminosalicylic acid dissolution behavior from granules coated by stearic acid—Eudragit L 100 mixed film in the first fluid and the second fluid.

As clearly shown in FIG. 1, in the first fluid of the disintegration test in JP, the medicinal substance was not released at all during at least 10 hours, but was released quickly in the second fluid of the disintegration test in JP after spending about 2.5 hours lag-time.

EXAMPLE 2

The layering granulation was carried out by adding the mixture of 40 g of theophylline, 50 g of sulfasalazine (arrival marker for large intestine: arriving a large intestine, which is decomposed into sulfapyridine and 5-aminosalicylic acid by enterobacteria, while the sulfapyridine is immediately absorbed.), 40 g of low substituted hydroxypropylcellose (grade: LH-20, available from The Shin-etsu Chemical Industry Co., Ltd.) and 200 g of D-mannitol to 50 g of Nonpareil with spraying 20% by weight of sucrose solution (solvent: mixture of water—ethanol (content of ethanol is 25% by weight)) as a binder, using a centrifugal fluidized bed coater (CF, made by Freund Industrial Co., Ltd.). The plain granule was obtained.

A coating solution was prepared by dissolving 24 g of Eudragit L 100 (available from Röhm Pharma) and 12 g of stearic acid into 700 g of ethanol. Using a centrifugal fluidized bed coater, 50 g of a plain granule were coated with the solution by spraying to obtain the granule coated with the mixed film of stearic acid—Eudragit L 100 having coating ratio of 67% by weight.

With respect to the coated granule obtained, the disintegration test was carried out with the first fluid (pH 1.2) and the second fluid (pH 6.8) of the disintegration test in JP according to the method of the disintegration test (puddle method) in JP, at 37° C. and at the rotation speed of 100 rpm.

Figure 2:
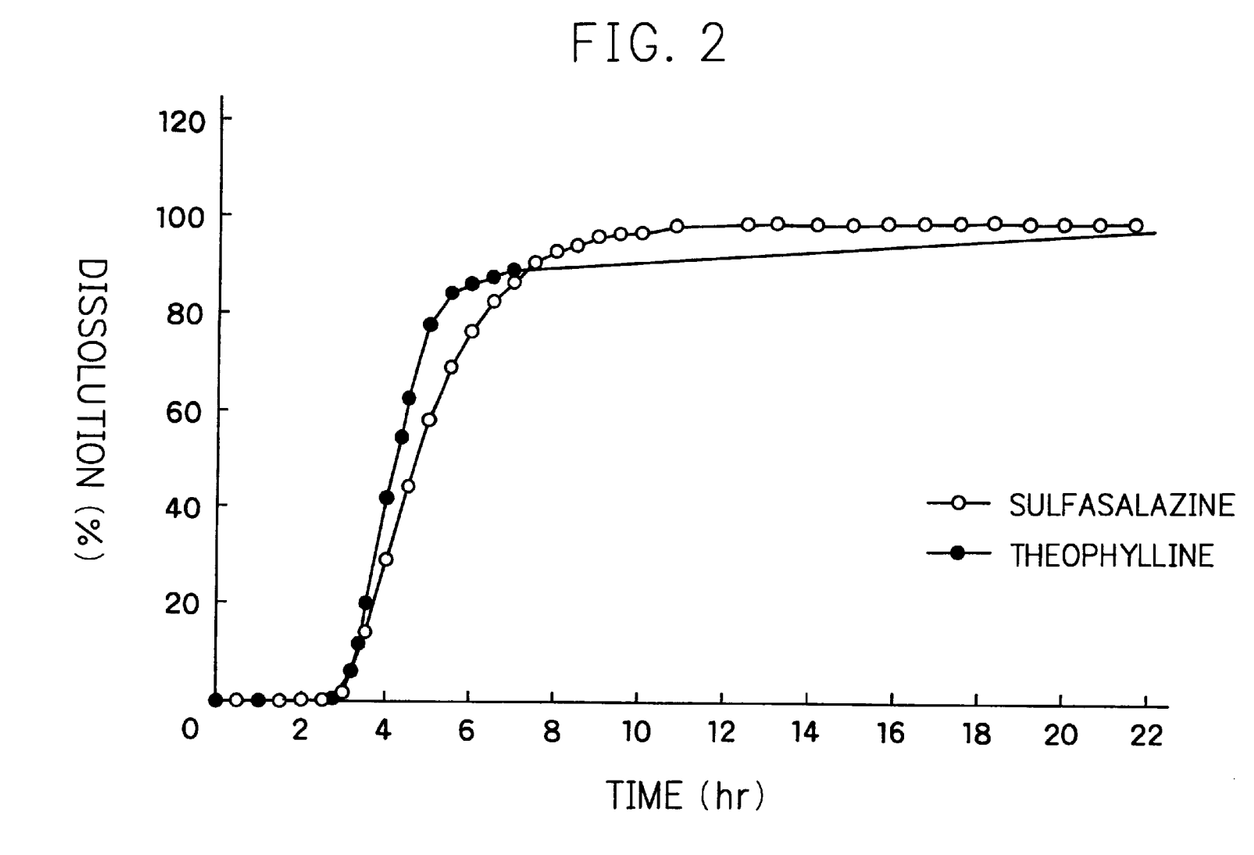
FIG. 2 is a graph showing each dissolution behavior of theophylline and sulfasalazine from granules coated by stearic acid—Eudragit L 100 mixed film in the second fluid.

In the first fluid, the medicinal substance was not released at all during at least 10 hours, but was released quickly in the second fluid after spending about 3 hours lag-time as shown in FIG. 2.

Comparetive Example 1

To 225 g of ethanol was dissolved 12.5 g of Eudragit L 100(available from Röhm Pharma), and dispersed 12.5 g of talc to obtain a coating solution. Using a centrifugal fluidized bed coater, 50 g of the plain granule of Example 2 were coated with the solution by spraying to obtain the granule coated with the film of Eudragit L 100 having coating ratio of 50% by weight.

With respect to the coated granule obtained, the disintegration test was carried out with the first fluid (pH 1.2) and the second fluid (pH 6.8) of the disintegration test in JP according to the method of the disintegration test (puddle method) in JP, at 37° C. and at the rotation speed of 100 rpm.

Figure 3:
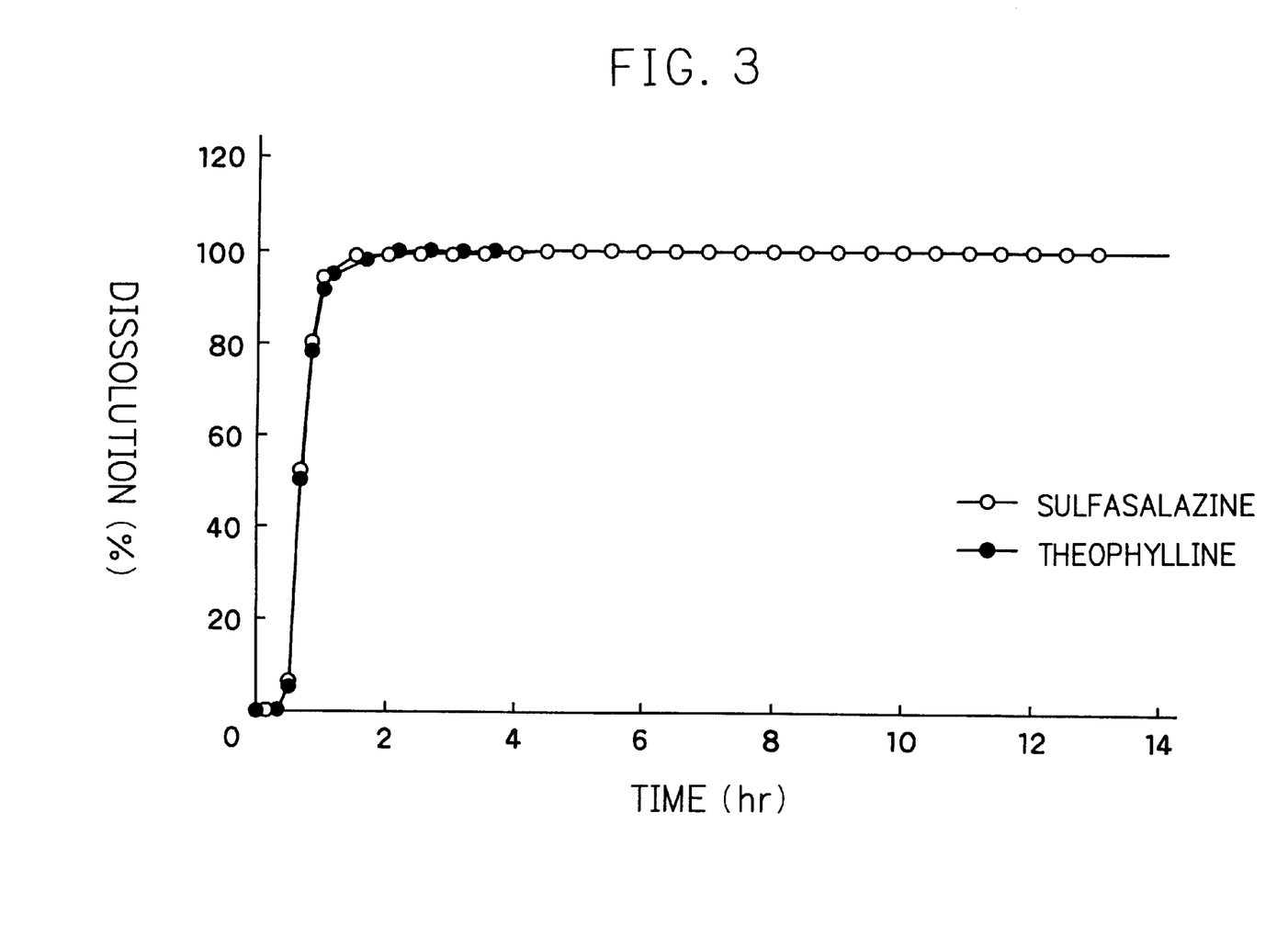
FIG. 3 is a graph showing each dissolution behavior of theophylline and sulfasalazine from granules coated by Eudragit L 100 in the second fluid.

In the first fluid, the medicinal substance was not released at all during at least 10 hours, but was released quickly in the second fluid immediately as shown in FIG. 3.

Experiment 1

Coated granules of Example 2 and Comparative Example 1 was orally administrated to four male beagle dogs which had fasted to determine the change of concentration in plasma of theophylline and sulfapyridine which is metabolite of sulfasalazine being arrival marker for a large intestine. The period of time until when theophylline and sulfapyridine appear in plasma is shown in TABLE 1.

TABLE 1

| Medicinal substance | Preparation of Example 2 | Preparation of Comparative Example 1 |
| --- | --- | --- |
| Theophylline | 4.0 ± 0.5 | 2.0 ± 0.0 |
| Sulfapyridine | 4.6 ± 0.1 | 4.0 ± 0.5 |

(n = 4 average ± S.E.)

As clearly shown in TABLE 1, for the coated granule of Comparative Example 1, theophylline appeared in plasma 2 hours after administration, more 2 hours later sulfapyridine being metabolite of sulfasalazine was observed. According to this, it was found that the granule was delivered to a large intestine 2 hours after discharging from the stomach, and that theophylline and sulfapyridine were released from the enteric granule in duodenum or small intestine.

While, for the granule of Example 2, theophylline and sulfapyridine appeared almost simultaneously in plasma about 4–4.6 hours after oral administration. According to this, it was found that theophylline and sulfapyridine were released in large intestine.

From the above-mentioned result, it was found that a medicinal substance could be delivered to specific site in the intestine, if the mixed film of stearic acid—Eudragit L 100 was used.

EXAMPLE 3

The layering granulation was carried out by adding the mixture of 200 g of 5-aminosalicylic acid and 30 g of low substituted hydroxypropylcellose (grade: LH-20, available from The Shin-etsu Chemical Industry Co., Ltd.) to 50 g of Nonpareil—103 (available from Freund Industrial Co., Ltd.) with spraying 20% by weight of sucrose solution (solvent: mixture of water—ethanol (content of ethanol is 25% by weight)) as a binder, using a centrifugal fluidized bed coater (CF, made by Freund Industrial Co., Ltd.). The plain granule was obtained.

A coating solution was prepared by dissolving 2.5 g of Eudragit L 100 (methacrylic acid.methylmethacrylate copolymer, available from Röhm Pharma) and 2.5 g of stearic acid (available from Snow Brand Milk Products Co., Ltd.) into 95 g of ethanol. Using a centrifugal fluidized bed coater, 50 g of a plain granule were coated with the solution by spraying to obtain granules coated with the mixed film of stearic acid—Eudragit L 100 having coating ratios of 30% and 40% by weight.

With respect to the coated granule obtained, the disintegration test was carried out with the second fluid (pH 6.8) of the disintegration test in JP according to the method of the disintegration test (puddle method) in JP, at 37° C. and at the rotation speed of 100 rpm. The result was shown in FIG. 4.

Figure 4:
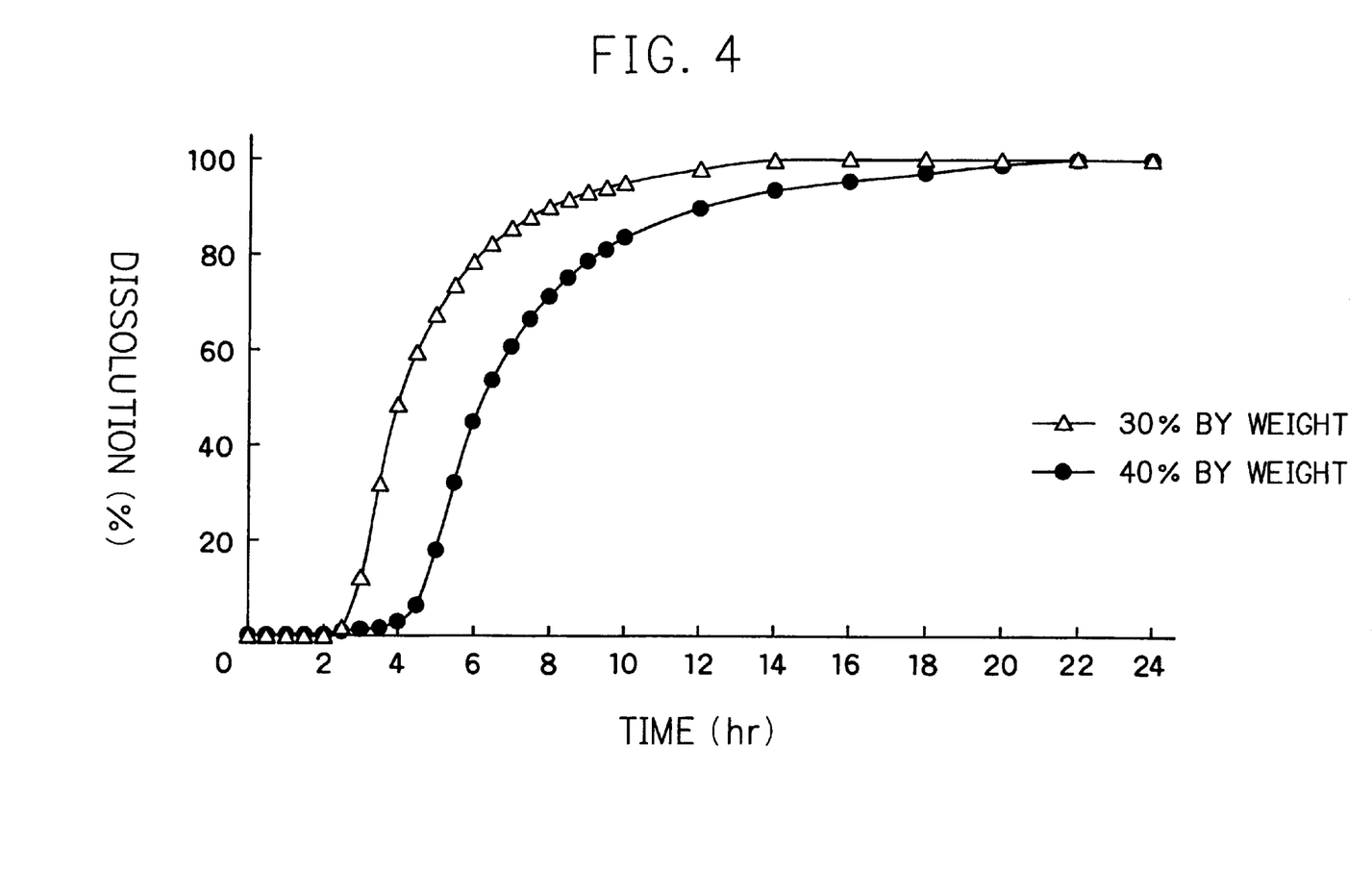
FIG. 4 is a graph showing the 5-aminosalicylic acid dissolution behavior from granules coated by stearic acid—Eudragit L 100 mixed film, wherein the rate of coating is 30 or 40% by weight, in the second fluid.

As clearly shown in FIG. 4, lag-time can be controlled by changing the coating ratio.

EXAMPLE 4

Using carboxymethylethylcellulose instead of Eudragit L-100, spray-coating was carried out with same manner in Example 3 to obtain granules coated with the mixed film of stearic acid—carboxymethylethylcellulose, having coating ratios of 120% and 140% by weight.

Figure 5:
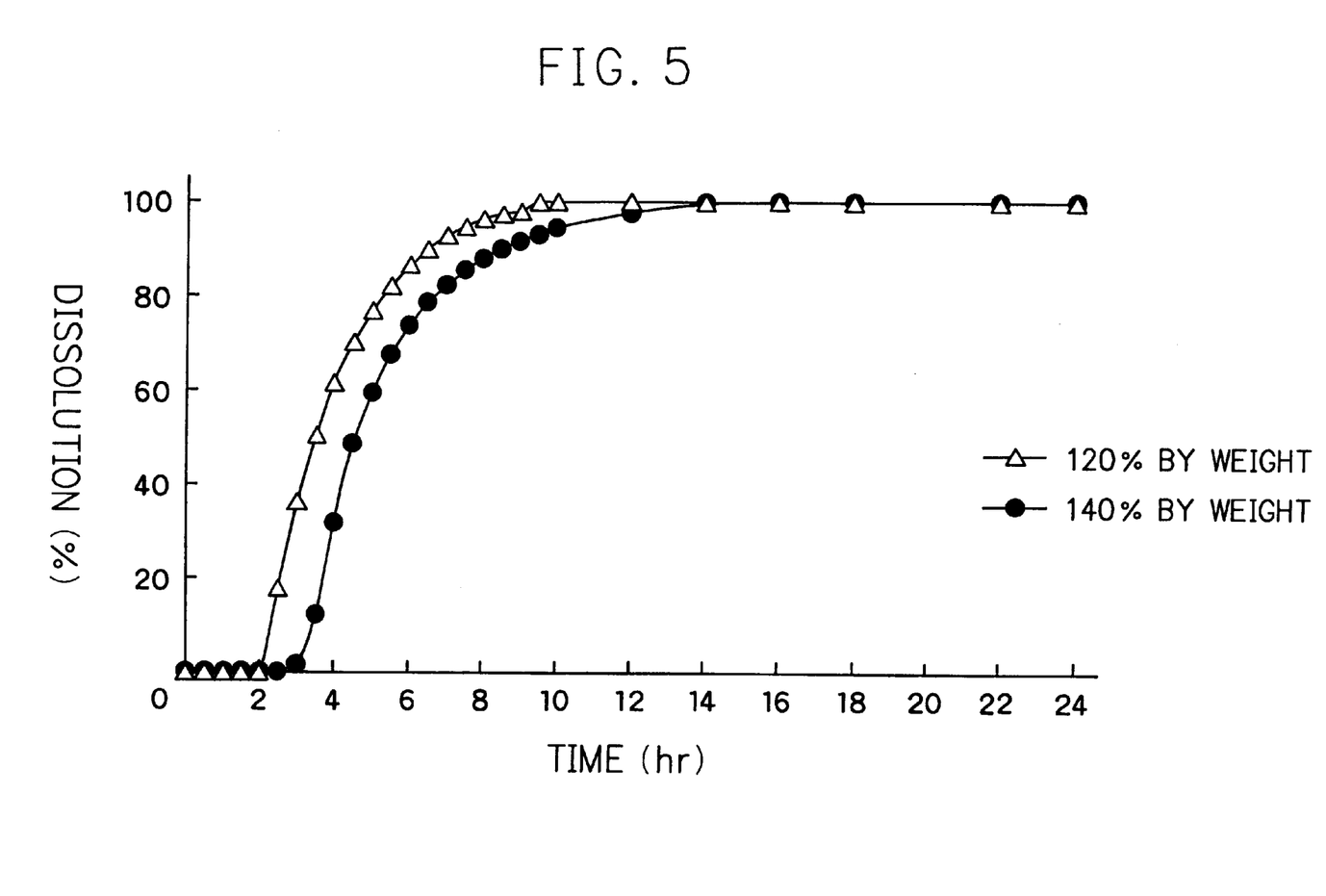
FIG. 5 is a graph showing the 5-aminosalicylic acid dissolution behavior from granules coated by stearic acid—carboxymethylethylcellulose mixed film, wherein the rate of coating is 120 or 140% by weight, in the second fluid.

With respect to the coated granule obtained, the dissolution test was carried out with the second fluid (pH 6.8) of the disintegration test in JP according to the method of the dissolution test (puddle method) in JP, at 37° C. and at the rotation speed of 100 rpm. The result was shown in FIG. 5.

EXAMPLE 5

Using palmitic acid instead of stearic acid, spray coating was carried out with same manner in Example 3 to obtain granules coated with the mixed film of palmitic acid—Eudragit L 100, having coating ratios of 50% and 60% by weight.

Figure 6:
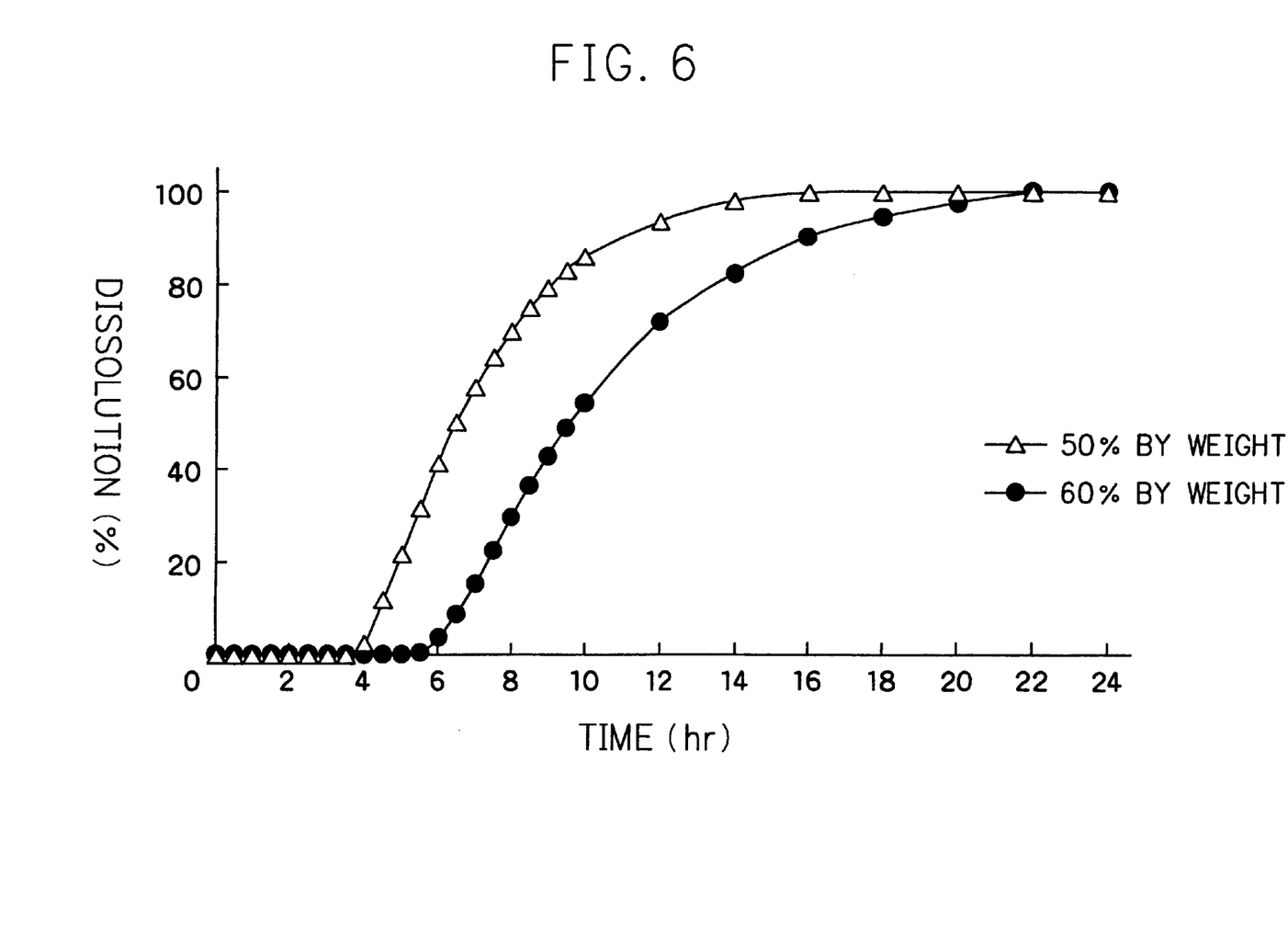
FIG. 6 is a graph showing the 5-aminosalicylic acid dissolution behavior from granules coated by palmitic acid—Eudragit L 100 mixed film, wherein the rate of coating is 50 or 60% by weight, in the second fluid.

With respect to the coated granule obtained, the dissolution test was carried out with the second fluid of the disintegration test in JP (pH 6.8) according to the method of the dissolution test (puddle method) in JP, at 37° C. and at the rotation speed of 100 rpm. The result was shown in FIG. 6.

INDUSTRIAL APPLICABILITY

Because the preparation of the present invention has a unique releasing behavior in that the preparation does not release medicinal substance at all in an acidic solution, but releases a medicinal substance quickly in a neutral or basic solution after a certain period of time (lag-time), the preparation can quickly release a medicinal substance when it reaches the desired site in the intestine after a certain period of time from discharge of the preparation from the stomach, by means of controlling the lag-time without releasing a medicinal substance in an acidic condition such as endogastric condition.

Therefore, the preparation of the present invention is useful for a local therapy of inflammatory disease in the intestine such as ulcerative colitis or crohn's disease, or an oral administrative therapy with a medicinal substance of a peptide which is apt to be decomposed chemically or enzymatically in any site except for a specific site in the intestine such as the large intestine, or with a medicinal substance whose absorption site in the intestine is limited, or the like, because a medicinal substance can be delivered selectively to a specific site in the intestine.

What is claimed is:

1. A unit dose composition capable of quickly releasing a medicinal substance at a targeted site in the intestine, comprising a core material containing a medicinal substance coated with a mixed film consisting essentially of a hydrophobic organic compound and an enteric polymer selected from the group consisting of an enteric acrylic copolymer, an enteric maleic copolymer and an enteric polyvinyl derivative, said mixed film having been deposited from solution, wherein the ratio of hydrophobic organic compound to enteric polymer is within a range of 30:70 to 80:20, and the coating ratio of the mixed film to core material is within a range of 20 to 300% by weight, wherein all of the core material in the composition has a coating with a ratio of hydrophobic organic compound to enteric polymer and a ratio of mixed film to core material which has been preselected so as to result in a product with a predetermined residency at acidic pH without release, and a predetermined residency at neutral or alkaline pH before release so as to quickly release the core material at a predetermined location in the intestinal tract of the subject to whom the composition is to be administered.

2. The unit dose composition of claim 1, wherein the hydrophobic organic compound is one or more compounds selected from the group consisting of a higher fatty acid having 6 to 22 carbon atoms which may have an unsaturated bond, a higher alcohol having 6 to 22 carbon atoms which may have an unsaturated bond, a triglyceride of the higher fatty acid having 6 to 22 carbon atoms which may have and unsaturated bond, and a natural fat which may be hydrogenated; and the enteric polymer is at least one polymer selected from the group consisting of an enteric celulose derivative, an enteric acrylic copolymer, an enteric maleic copolymer, and an enteric polyvinyl derivativate.

3. A unit dose composition capable of quickly releasing a medicinal substance at a targeted site in the intestine, comprising a core material containing a medicinal substance coated with a mixed film consisting essentially of a hydrophobic organic compound and an enteric polymer, said mixed film having been deposited from solution, wherein the ratio of hydrophobic organic compound to enteric polymer is within a range of 30:70 to 80:20, and the coating ratio of the mixed film to core material is within a range of 20 to 100% by weight, wherein all of the core material in the composition has a coating with a ratio of hydrophobic organic compound to enteric polymer and a ratio of mixed film to core material which has been preselected so as to result in a product with predetermined residency at acidic pH before release so as to quickly release the core material at a predetermined location in the intestinal tract of the subject to whom the composition is to be administered.

4. The unit dose composition of claim 1, wherein the hydrophobic organic compound is stearic acid and the enteric polymer is methacrylic acid methyl methacrylate copolymer.

5. The unit dose composition of claim 3, wherein the hydrophobic organic compound is one or more compounds selected from the group consisting of a higher fatty acid having 6 to 22 carbon atoms which may have an unsaturated bond, a higher alcohol having 6 to 22 carbon atoms which may have an unsaturated bond, a triglyceride of the higher fatty acid having 6 to 22 carbon atoms which may have an unsaturated bond, and a natural fat which may be hydrogenated; and the enteric polymer is at least one polymer selected from the group consisting of an enteric cellulose derivative, an enteric acrylic copolymer, an enteric maleic copolymer, and an enteric polyvinyl derivative.

6. The unit dose composition of claim 1, wherein the coating ratio of the mixed film of hydrophobic organic compound—enteric polymer is within a range of 20 to 100% by weight.

7. The unit dose composition of claim 1, wherein the medicinal substance is not released during 5 hours in the first fluid of the disintegration test in Japanese Pharmacopoeia XIII and is not released during at least 2 hours in the second fluid of the disintegration test in Japanese Pharmacopoeia XIII.

8. The unit dose composition of claim 3, wherein the hydrophobic organic compound is stearic acid and the enteric polymer is methacrylic acid methyl methacrylate.

9. The unit dose composition of claim 2, wherein the higher fatty acid having 6 to 22 carbon atoms which may have an unsaturated bond is at least one fatty acid selected from the group consisting of stearic acid, lauric acid, myristic acid, palmitic acid and behenic acid; the higher alcohol having 6 to 22 carbon atoms which may have an unsaturated bond is at least one higher alcohol selected from the group consisting of lauryl alcohol, myristyl alcohol, cetyl alcohol, stearyl alcohol and behenyl alcohol; the triglyceride of the fatty acid having 6 to 22 carbon atoms which may have an unsaturated bond is at least one triglyceride selected from the group consisting of glyceryl tristearate, glyceryl trimyristate, glyceryl tripalmitate and glyceryl trilaurate; the natural fat which may be hydrogenated is at least one natural fat selected from the group consisting of hydrogenated castor oil, hydrogenated coconut oil, and beef tallow; the enteric acrylic copolymer is at least one copolymer selected from the group consisting of styrene.acrylic acid copolymer, methyl acrylate.acrylic acid copolymer, methyl acrylate-.methacrylic acid copolymer, butyl acrylate.tyrene.acrylic acid copolymer, methacrylic acid.methyl methacrylate copolymer, methacrylic acid.ethyl acrylate copolymer, and methyl acrylate.methacrylic acid.octyl acrylate copolymer; the enteric maleic copolymer is at least one copolymer selected from the group consisting of vinylacetate.maleic acid anhydride copolymer, styrene.maleic acid anhydride copolymer, styrene.maleic acid monoester copolymer, vinylmethylether.maleic acid anhydride copolymer, ethylene.maleic acid anhydride copolymer, vinylbutylether.maleic acid anhydride copolymer, acrylonitrile.methyl acrylate.maleic acid anhydride copolymer, and butyl acrylate.styrene.maleic acid anhydride copolymer; and the enteric polyvinyl derivative is at least one derivative selected from the group consisting of polyvinyl alcohol phthalate, polyvinylacetal phthalate, polyvinyl butylate phthalate and polyvinylacetoacetal phthalate.

10. A method for preparing a composition capable of releasing a medicinal substance at a targeted site in the intestinal tract of the subject to which the composition is to be administered, comprising:

causing a mixed film consisting essentially of a hydrophobic organic compound and an enteric polymer to be deposited onto a core material containing a medicinal substance, said mixed film being deposited from a coating composition comprising the hydrophobic organic compound and the enteric polymer, both dissolved in a solvent, wherein the ratio of the hydrophobic organic compound to the enteric polymer in the coating composition and the amount of mixed film deposited onto the core material are controlled so as to result in a product with a predetermined residency at acidic pH without release, and a predetermined residency at neutral or alkaline pH before release so as to release the core material at a predetermined location in the intestinal tract of the subject to whom the composition is to be administered.

11. A method in accordance with claim 10, wherein the mixed film is deposited onto the core material by spray-coating the coating composition onto the core material.

12. A method in accordance with claim 10, wherein the hydrophobic organic compound is at least one selected from the group consisting of a higher fatty acid having 6 to 22 carbon atoms which may have an unsaturated bond, a higher alcohol having 6 to 22 carbon atoms which may have an unsaturated bond, a triglyceride of the higher fatty acid having 6 to 22 carbon atoms which may have an unsaturated bond, and a natural fat which may be hydrogenated; and the enteric polymer is one or more selected from the group consisting of an enteric cellulose derivative, an enteric acrylic copolymer, an enteric maleic copolymer, and an enteric polyvinyl derivative.

13. A method in accordance with claim 12, wherein the higher fatty acid having 6 to 22 carbon atoms which may have an unsaturated bond is at least one selected from the group consisting of stearic acid, lauric acid, myristic acid, palmitic acid, and behenic acid; the higher alcohol having 6 to 22 carbon atoms which may have an unsaturated bond is at least one selected from the group consisting of lauryl alcohol, myristyl alcohol, cetyl alcohol, stearyl alcohol, and behenyl alcohol; the triglyceride of the fatty acid having 6 to 22 carbon atoms which may have an unsaturated bond is at least one selected from the group consisting of glyceryl tristearate, glyceryl trimyristate, glyceryl tripalmitate, and glyceryl trilaurate; the natural fat which may be hydrogenated is at least one selected from the group consisting of hydrogenated castor oil, hydrogenated coconut oil, and beef tallow; the enteric cellulose derivative is at least one selected from the group consisting of hydroxypropylmethylcellulose acetate succinate, hydroxypropylmethylcellulose phthalate, hydroxymethylethylcellulose phthaiate, cellulose acetate phthalate, cellulose acetate succinate, cellulose acetate maleate, cellulose benzoate phthalate, cellulose propionate phthalate, methylcellulose phthalate, carboxymethylethylcellulose, and ethylhydroxyethylcellulose phthalate; the enteric acrylic copolymer is at least one selected from the group consisting of styrene.acrylic acid copolymer, methyl acrylate.acrylic acid copolymer, methyl acrylate.methacrylic acid copolymer, butyl acrylate.styrene-.acrylic acid copolymer, methacrylic acid.methyl methacrylate copolymer, methacrylic acid.ethyl acrylate copolymer, and methyl acrylate.methacrylic acid.octyl acrylate copolymer; the enteric maleic copolymer is at least one selected from the group consisting of vinylacetate.maleic acid anhydride copolymer, styrene.maleic acid anhydride copolymer, styrene.maleic acid monoester copolymer, vinylmethylether.maleic acid anhydride copolymer, ethylene.maleic acid anhydride copolymer, vinilbutylether.maleic acid anhydride copolymer, acrylonitrile.methyl acrylate.maleic acid anhydride copolymer, and butyl acrylate.styrene.maleic acid anhydride copolymer; and the enteric polyvinyl derivative is at least one selected from the group consisting of polyvinyl alcohol phthalate, polyvinylacetal phthalate, polyvinyl butylate phthalate, and polyvinylacetoacetal phthalate.

14. A method in accordance with claim 10, wherein the hydrophobic organic compound is stearic acid and the enteric polymer is methacrylic acid methyl methacrylate copolymer.

15. A method in accordance with claim 10, wherein the mixing ratio of the amount of the hydrophobic organic compound to the amount of the enteric polymer in the mixed film of hydrophobic organic compound—enteric polymer is within a rnge of 30:70 to 80:20.

16. A method in accordance with claim 10, wherein the coating ratio of the mixed film to core material is within a range of 20 to 100% by weight.

17. A method in accordance with claim 10, wherein the ratio of the hydrophobic organic compound to the enteric polymer in the coating composition and the amount of mixed film deposited onto the core material are controlled so as to result in a product which does not release the medicinal substance during 5 hours in the first fluid of the disintegration test in Japanese Pharmacopoeia XIII and does not release the medicinal substance for at least 2 hours in the second fluid of the disintegration test in Japanese Pharmacopoeia XIII.

18. A unit dose composition in accordance with claim 1, wherein said mixed film consists of said hydrophobic organic compound and said enteric polymer and, optionally, one or more agents selected from the group consisting of coloring agents, masking agents, plasticizers, lubricants, vehicles, disintegrants, binders, surface active agents, aromatics, corrigents, and solubilizing agents.

19. The unit dose composition of claim 3, wherein the medicinal substance is not released during 5 hours in the first fluid of the disintegration test in Japanese Pharmacopoeia XIII and is not released during at least 2 hours in the second fluid of the disintegration test in Japanese Pharmacopoeia XIII.

20. The unit dose composition of claim 1, wherein the predetermined location in the intestinal tract is the ileum, the ascending colon or the transverse colon.

21. A method in accordance with claim 10, wherein the predetermined location in the intestinal tract is the ileum, the ascending colon or the transverse colon.

22. The unit dose composition of claim 5, wherein the higher fatty acid having 6 to 22 carbon atoms which may have an unsaturated bond is at least one fatty acid selected from the group consisting of stearic acid, lauric acid, myristic acid, palmitic acid and behenic acid; the higher alcohol having 6 to 22 carbon atoms which may have an unsaturated bond is at least one higher alcohol selected from the group consisting of lauryl alcohol, myristyl alcohol, cetyl alcohol, stearyl alcohol and behenyl alcohol; the triglyceride of the fatty acid having 6 to 22 carbon atoms which may have an unsaturated bond is at least one triglyceride selected from the group consisting of glyceryl tristearate, glyceryl trimyristate, glyceryl tripalmitate and glyceryl trilaurate; the natural fat which may be hydrogenated is at least one natural fat selected from the group consisting of hydrogenated castor oil, hydrogenated coconut oil, and beef tallow; the enteric cellulose derivative is at least one derivative selected from the group consisting of hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose and ethylhydroxyethylcellulose phthalate; the enteric acrylic copolymer is at least one copolymer selected from the group consisting of styrene.acrylic acid copolymer, methyl acrylate.acrylic acid copolymer, methyl acrylate.methacrylic acid copolymer, butyl acrylate.styrene.acrylic acid copolymer, methacrylic acid.methyl methacrylate copolymer, methacrylic acid.ethyl acrylate copolymer, and methyl acrylate.methacrylic acid.octyl acrylate copolymer; the enteric maleic copolymer is at least one copolymer selected from the group consisting of vinylacetate.maleic acid anhydride copolymer, styrene.maleic acid anhydride copolymer, styrene.maleic acid monoester copolymer, vinylmethylether.maleic acid anhydride copolymer, ethylene.maleic acid anhydride copolymer, vinylbutylether.maleic acid anhydride copolymer, acrylonitrile.methyl acrylate.maleic acid anhydride copolymer, and butyl acrylate.styrene.maleic acid anhydride copolymer; and the enteric polyvinyl derivative is at least one derivative selected from the group consisting of polyvinyl alcohol phthalate, polyvinylacetal phthalate, polyvinyl butylate phthalate and polyvinylacetoacetal phthalate.

23. A unit dose composition in accordance with claim 3, wherein said mixed film consists of said hydrophobic organic compound and said enteric polymer and, optionally, one or more agents selected from the group consisting of coloring agents, masking agents, plasticizers, lubricants, vehicles disintegrants, binders, surface active agents, aromatics, corrigents, and solubilizing agents.

24. The unit dose composition of claim 3, wherein the predetermined location in the intestinal tract is the ileum, the ascending colon or the transverse colon.

25. A method in accordance with claim 10, wherein said mixed film consists of said hydrophobic organic compound and said enteric polymer and, optionally, one or more agents selected from the group consisting of coloring agents, masking agents, plasticizers, lubricants, vehicles, disintegrants, binders, surface active agents, aromatics, corrigents and solubilizing agents.

* * * * *